United States Patent [19]

Murofushi et al.

[11] 4,229,440
[45] Oct. 21, 1980

[54] PHARMACEUTICAL COMPOSITION CONTAINING THE POLYSACCHARIDE KGF-C AS ACTIVE INGREDIENT

[75] Inventors: Mitsugu Murofushi; Kuniaki Sasaki, both of Yokohama; Michio Shiomi, Isehara; Yoshio Uchida, Hiratsuka; Tokihisa Hattori, Mishima; Keniti Takeda, Machida, all of Japan

[73] Assignee: Fujiya Confectionery Company Limited, Tokyo, Japan

[21] Appl. No.: 963,967

[22] Filed: Nov. 27, 1978

[51] Int. Cl.$^3$ .................. A61K 31/735; C08B 37/00
[52] U.S. Cl. ........................................ 424/180; 536/1
[58] Field of Search ............................ 536/1; 424/180

[56] References Cited

U.S. PATENT DOCUMENTS

| | | | |
|---|---|---|---|
| 3,855,201 | 12/1974 | Buchner et al. | 536/1 |
| 3,988,313 | 10/1976 | Bouniot | 536/1 |

OTHER PUBLICATIONS

Kooiman; "Chemical Abstracts", vol. 69, 1968, p. 44,135(b).

*Primary Examiner*—Johnnie R. Brown
*Attorney, Agent, or Firm*—Browdy and Neimark

[57] ABSTRACT

KGF-C is obtained by grinding kefir grain, adding water to the ground kefir grain and heating, homogenizing the mixture and centrifuging it, adding ethanol to the obtained supernatant to obtain a precipitate, dissolving the precipitate into water, purifying the obtained liquid and freeze-drying the remaining liquid. The obtained KGF-C is soluble in water and is composed of polysaccharide as principal component and contains a very small amount of nitrogenous component, and, as sugar composition, is composed of glucose and galactose in the ratio 1:1. This KGF-C has strong antitumor action by oral administration.

1 Claim, 1 Drawing Figure

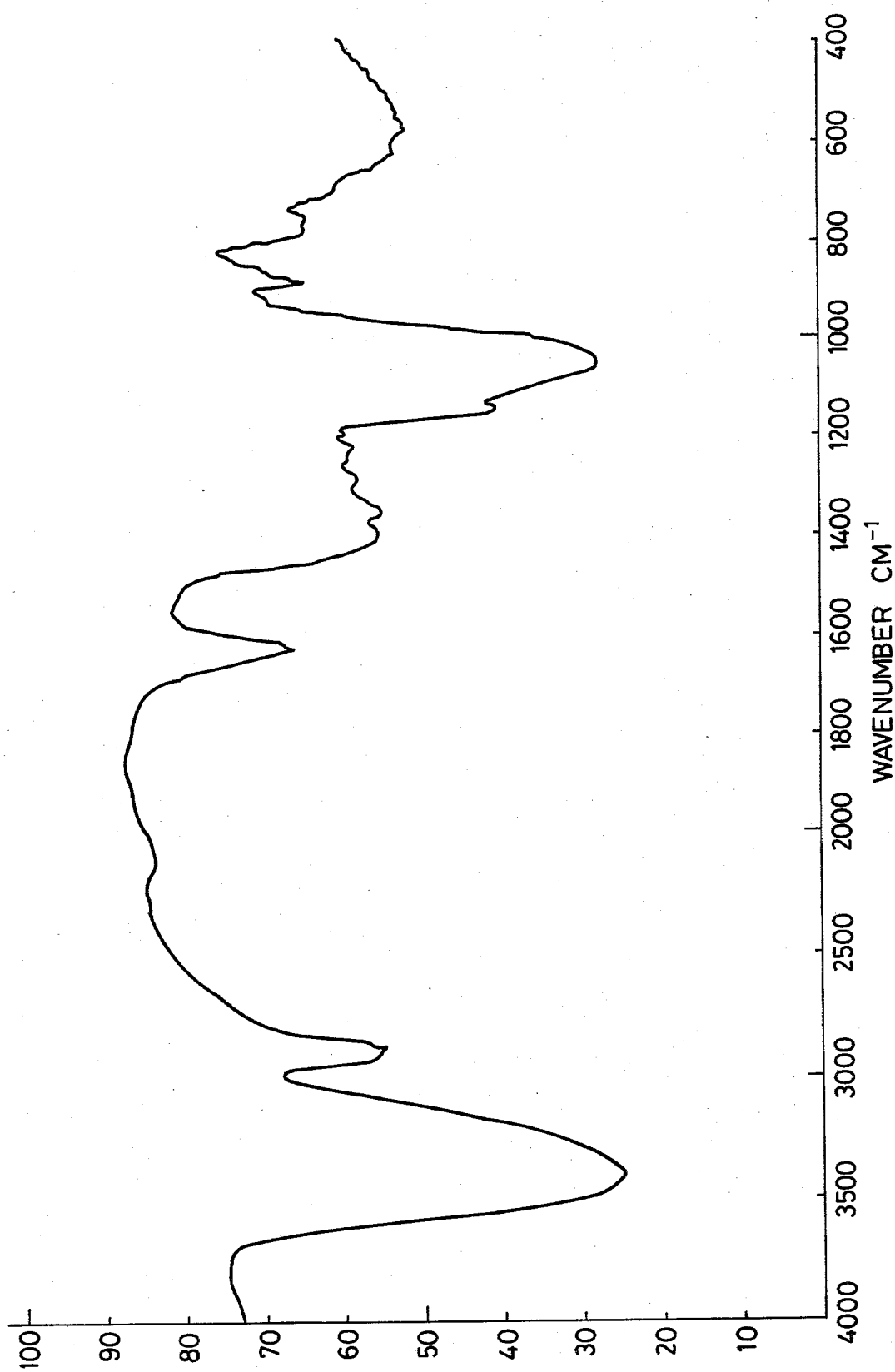

PHARMACEUTICAL COMPOSITION CONTAINING THE POLYSACCHARIDE KGF-C AS ACTIVE INGREDIENT

The present invention relates to KGF-C obtained from kefir grain, and more particularly to KGF-C having antitumor property.

Heretofore a manner of antitumor agents have been known, but almost none of such prior art agents have been put to practical use. This is, in most cases, caused by adverse reactions and toxicity thereof, as is obvious from the fact that, for example, in the case of an antitumor agent produced by microorganisms, almost all of such microorganisms are Gram negative bacteria and the majority thereof are pathogenic bacteria. Another cause is that there is no activity in the case of oral administration.

The present invention has an object to overcome such drawbacks, and studies having been pursued for seeking a strong antitumor agent which has a low toxicity and also is able to be orally administered, and as a result it was discovered that the soluble substance of kefir grain completely satisfied the above conditions, and therefore the present invention has been completed on the basis of this discovery.

BRIEF DESCRIPTION OF DRAWING

The FIGURE shows infrared absorption spectrum of KGF-C.

The present invention is an antitumor agent obtained by isolating a soluble fraction from kefir grain containing said soluble substance as an effective component. The kefir grain is a fermentation source (starter) of kefir, a kind of fermented milk which is a traditional food in Caucasus Mountains area in Soviet Union territory, and it may also be called kefir seed or kefir grain.

Kefir grain is a mass of bacteria which is elastic and has a whitish to yellowish color and normally is of spherical grain of a bean size and composed of a mixture of at least seven or eight kinds of microbes and the products thereof, the microbes being the lactic acid bacteria such as Streptococcus lactis and Lactobacillus brevis etc. and yeasts such as genuses Saccharomyces and Torula etc. The microorganisms isolated from kefir grain up to now are classified as follows: *Streptococcus cremoris, Streptococcus citrovorus, Streptococcus paracitrovorus, Streptococcus diacetilactis, Lactobacillus acidophilus, Lactobacillus casei, Lactobacillus caucasicus, Leuconostoc kefyr, Saccharomyces lactis, Saccharomyces carlsbergensis, Torulopsis kefyr, Candida pseudotropicalis, Candida tenuis, Bacillus subtilis, Acetobacter rancens,* strain of genus Mycoderma and so forth, besides said lactic acid bacteria above mentioned.

However, the main microorganisms are the lactic acid bacteria and yeasts, and although the kind and number of these microbes may slightly vary according to the circumstances and culture conditions, they usually show a constant value. As these microorganisms maintain symbiotic relations between them, even if these are separated individually and subsequently cultured separately and then mixed together, kefir grain can not be obtained. However, by subjecting kefir grain itself to a successive transfer culture in the same manner as in the case of a single strain, kefir grain has been successfully completely cultured by the successive transfer culture in the same medium and culture conditions as in the case of usual lactic acid bacteria and it was confirmed that the kefir grain soluble substance used in the present invention was always obtained from kefir grain thus obtained. Also, whatever type of kefir grain it may be, kefir grain can be completely cultured by the successive transfer culture, and at the same time it was confirmed that every kefir grain soluble substance obtained from the resulting kefir grain showed antitumor property without exceptions, thus resulting in completion of the present invention. Namely, the present invention always permits the production of antitumor agent whatever kind of kefir grain is used in so far as such a kefir grain is used that it contains, as main microorganism, lactic acid bacteria containing the lactic acid bacteria having capsule forming ability and yeasts as described above. Accordingly, with respect to the present invention using microorganisms, the microorganisms, as raw material, are easily available and also, viewed from the aspect of the production of antitumor agent, it has been proved that there are not any problems in relation to possibility of repetition and reproducibility. In addition, since it is possible to handle kefir grain as a single strain by culturing continuously under a certain condition, this was named as kefir grain F20 and the deposit application thereof was filed with the Fermentation Research Institute, Agency of Industrial Science and Technology, but this application was not accepted because it was a mixed strain. However, as described above, kefir grain can be obtained very easily, and therefore even from the viewpoint of microorganism the disclosure about kefir grain in the present specification is complete, and this kefir grain has been deposited with the American Type Culture Collection under the deposition number of ATCC No. 40006.

Kefir grain can freely be grown and propagated in either natural or synthetic media as in the case of lactic acid bacteria if there is a milk material in said medium. In the case of the natural medium, kefir grain is mixed with, for example, homogenized sterilized milk or skim milk in an amount of 3–8%, and it is incubated with occasional shaking at a temperature of 10°–40° C., preferably 16°–25° C. for 5–50 hours, preferably 8–24 hours, and then in case of attainment of acidity of 0.8–1.0% this cultured mixture is cooled to a temperature of 12°–16° C. and kefir grain is filtered off from the mixture. The thus resulting filtrate is kefir. The obtained kefir grain is again added with new milk raw material and the above described process is repeated. Like this, kefir grain can be produced in a large amount. Also, in case of the synthetic medium, kefir grain can be cultured by the use of a liquid medium containing, for example, peptone, yeast extract, malt extract, glucose, lactose and inorganic substance etc., and more particularly liquid medium containing a vegetable juice such as tomato juice and so forth or a fruit juice such as orange juice and grape juice.

The thus obtained incubation mixture is filtered by means of a wire screen to collect kefir grain. The kefir grain is thoroughly washed by water, and after drying for example by such as freeze-drying, etc. or as it is without any drying treatments, it is ground, and the resulting ground matter is added with water and heated at about 70° C., and treated by a homogenizer and subjected to a centrifugal separation, and the produced supernatant is collected, and the precipitate is repeatedly subjected to the similar hot water treatment and centrifugal treatment more than two times, thereby obtaining the supernatant, which is added to the previously obtained supernatant, and thus collected supernatant liquid is purified by the combination of ion-exchange resin treatment, dialysis and so forth, and from the purified liquid, lustrous white cotton-like powder is yielded by solvent precipitation, freeze-drying and so forth, and this resulting powder is called kefir grain soluble substance.

The thus obtained kefir grain soluble substance which is an available component of the present invention has been named KGF-C. The present substance KGF-C has the following physical and chemical properties:

Physical and Chemical Properties of KGF-C (1) Appearance: Tasteless and odorless white powder having a little hygroscopicity.
(2) Solubility: Soluble in water and pyridine and insoluble in alcohol, glacial acetic acid, acetone, benzene, carbon tetrachloride, chloroform, ether and tetrahydrofuran.
(3) The pH of 1% aqueous solution is 6.89.
(4) Sugar qualitative reaction: With respect to the 1% aqueous solution and liquid hydrolyzate thereof, Molish and Tollens tests are carried out and obtained following results:

|  | 1% aqueous solution | 0.1% liquid hydrolyzate |
|---|---|---|
| Molish reaction | + | + |
| Tollens reaction | − | + |

(5) Specific optical rotation: $(\alpha)_D^{20} = +62.0°$ (C=1, water)
(6) Sugar content: 99% is shown by phenol sulfuric acid method. KGF-C is composed of polysaccharide as principal component, and contains a very small amount of nitrogenous component.
(7) Sugar composition: KGF-C was hydrolyzed by 0.5% $H_2SO_4$ at 110° C. for 5 hours and then the sugar composition was determined by thin layer chromatography and gas chromatography, and the results showed that it composed of glucose and galactose in the ratio 1:1.
(8) Ultraviolet absorption spectrum: No particular absorption is observed.
(9) Infrared absorption spectrum: As shown in FIG. 1, the particular absorption bands are shown.
(10) Elemental analysis: C: 41.83%, H: 6.19%, N: 0.20%, S: below 0.2%, P: below 0.2%.

The present invention is an antitumor agent characterized by containing kefir grain soluble substance as principal component.

The most important feature of the antitumor agent of the present invention is that it has scarcely any toxicity and has a very high antitumor activity and is able to be administered orally. In the case of oral administration, adverse reaction is generally low and therefore administration of this type is desirable, but there has heretofore scarcely been any carcinostatic substance which can be orally administered, and therefore the present invention is a very unique one. Since it is a matter of course that the antitumor agent of the present invention can be parenterally administered, it can be said that this antitumor agent is a very new type of medicine which has not been present so far and shows a notable inhibitory activity in either the case of oral or parenteral administration. As will be apparent from the facts described hereinafter, it has been found that the present antitumor agent has a notable inhibition against solid transplantable cancer and solid transplantable tumor even by oral administration as a result of animal experiment, and also found that even in the case of intraperitoneal administration, there is a very strong antitumor action without any adverse reactions. Moreover, as the antitumor agent of the present invention has scarcely any toxicity, therefore it can be said to be an effective antitumor agent.

In the practical use of this antitumor agent, in either the case of oral or parenteral administration, it can be used in the form of conventional pharmaceutical preparations. It can be administered in conventional pharmaceutical forms, for example, solutions, suspensions, powders, granules, capsules or tablets etc., and also it is possible as desired to be associated with conventional pharmaceutically acceptable additives such as bonding agent, lubricant, dispersing agent, suspension, emulsifier, diluent, buffer agent, antioxidant and bacteria inhibitor, etc.

Hereinafter, embodiments of the present invention will be successively shown in relation to production example for production of kefir grain soluble substance, practical example for showing antitumor property and experimental example for showing low toxities.

PRODUCTION EXAMPLE

Production of Kefir Grain Soluble Substance 10 kg of skim milk is homogenized, and sterilized at 80° C. for 20 minutes and then cooled to 10° C. The resulting material is added with 1 kg (10%) of kefir grain which was produced by training culture of kefir grain F20,ATCC No. 40006 at a low temperature, and then the mixture is stirred for five minutes and thereafter it is stirred gently for five minutes at an interval of four hours while effecting fermentation at 10° C. for 45 hours, with the result that the acidity of the mixture reaches 0.94%. At this point, the fermentation is stopped, the resulting kefir grain is filtered off through a wire screen with about 0.8 mm meshes to obtain kefir grain.

The obtained kefir grain is well washed with distilled water and freeze-dried and the dried matter is ground. The ground matter is added with distilled water of an amount of about 30-40 times by volume of said ground matter and heated at 70° C. for 15 minutes, and then subjected to treatment of homogenizer and then to centrifugal separation at 10,000 rpm for 20 minutes and thereafter the resulting supernatant is collected. The separated precipitate is added with distilled water and again heated at 70° C. for 15 minutes, and then subjected to homogenizer treatment and centrifugal separation similar to the above, and subsequently such operation is carried out two times, and thus the heating extraction and centrifugal treatment are carried out three times in all, and the obtained supernatant liquids are combined, and the combined supernatant is added with ethanol of an amount of three times by volume of said liquid to obtain the precipitate. The precipitate is added with distilled water and heated to dissolve it, and subjected to the centrifugal separation, and the resulting supernatant liquid is collected. Such operation is repeated three times and thus obtained supernatant liquid is passed through Amberlite IRA 400 to purify it and then subjected to dialysis by means of cellophane tube and subsequently to freeze-drying.

Thus obtained dried substance is lustrous white cotton-like matter. 5.6 g of the freeze-dried matter was obtained from 500 g of the washed kefir grain.

PRACTICAL EXAMPLE

Antitumor Action Against Ehrlich Ascites Solid Tumor and Solid Tumor of Sarcoma 180 of Mouse (1) Production of Antitumor Agent
  (i) Kefir grain soluble substance (KGF-C) produced in said production example is suspended in physiological sodium chloride solution and the resulting suspension is used for intraperitoneal administration.
  (ii) KGF-C produced in said production example is used for enteral administration as it is or in capsules.

(2) Antitumor Action
  (i) Kind of Tumor and Inoculation Method
  The tumor cells used for the experiment were Ehrlich ascites tumor cells and sarcoma 180 cells, and in either case these cells are such ones prepared as follows: the cells were inoculated in the peritoneal cavity of 5-weeks-old male mouse of $ddY_F$ and ICR-SLC, and these inoculated cells were transplanted at an interval of one week as ascites type. In the experiment, the cells in the ascites were taken out one week after the inoculation, and these cells were added to the physiological saline solution to obtain respectively 2 kinds of said solution, one containing about two million of Ehrlich ascites tumor cells and the other containing about ten million of sarcoma 180 cells, and then a test mouse was given a subcutaneous injection into right lower portion of flank of 0.2 ml of said prepared saline solution.

(ii) Administration Method of KGF-C
  In the experiment of oral administration, 0.02 and 0.1% of KGF-C powder are respectively mixed in a standard powdered animal feed or drinking water, and the resulting mixture was left to free ingestion of the test mouse. The period of administration was (a) from the time of the transplantation to the time of the extraction of tumor, (b) from before the transplantation to the time of the extraction of tumor or (c) only before the transplantation. For the mice of control group, the standard powdered feed for breeding was fed. In the experiment of intraperitoneal administration, 0.2 ml of the physiological saline solution in which KGF-C powder was dissolved and suspended was administered into the peritoneal cavity of mouse. The administration began respectively (a) from twenty-four hours after the transplantation, (b) from seven days after the transplantation or (c) from before the transplantation, and said saline solution was administered respectively (A) every day, (B) every other day or (C) every fourth day. For the mice of control group the physiological saline solution was administered.

(iii) Calculation of Inhibition Rate
  About three to five weeks, and seven weeks after the transplantation, the mouse was sacrificed each time, and the propagated solid tumor was extracted and the weight of removed tumor was measured, and the inhibition rate was calculated according to the following formula:

Inhibition rate $= (C - T)/C \times 100$ (wherein, C: Average tumor weight of the control group, T: Average tumor weight of the test group)

(iiii) Results
  The above test results relating to antitumor activity of KGF-C are summed up as shown in Table 1 in the case of the oral administration and Table 2 in the case of the intraperitoneal administration.

TABLE I

Result in the Oral Administration Experiment of KGF-C

| Test | Tumor | Mouse | Amount of Administration % *3 | Period of Administration *4 | Extraction Day *5 | Dead Number | Average Tumor Weight g | Inhibition Rate % |
|---|---|---|---|---|---|---|---|---|
| 1 | *1 S-180 | ICR | 0.1 Control | +35 " | 35 " | 0/10 " | 1.019 5.435 | 81.3 — |
| 2 | S-180 | ICR | 0.1 0.02 Control | +29 " " | 29 " " | 0/10 " " | 1.657 3.560 5.964 | 72.2 40.3 — |
| 3 | *2 E.C. | $ddY_F$ | 0.1 0.1 Control | +24 −7 +24 | 24 " " | 0/9 " " | 3.537 4.004 8.655 | 59.1 53.7 — |
| 4 | E.C. | ICR | 0.1 0.02 Control | +23 " " | 23 " " | 0/9 " 0/10 | 0.609 0.754 1.250 | 51.3 39.7 " |

*1 Sarcoma S-180 tumor cell
*2 Ehrlich ascites tumor cell
*3 Mixing rate of feed
*4 (−): Before transplantation, (+): After transplantation
*5 Number of day from after transplantation to extraction

TABLE 2

Result in the Intraperitoneal Administration Experiment of KGF-C

| Test | Tumor | Mouse | Amount of Administration mg *3 | Frequency of Administration | Start of Interval | Extraction Administration *4 | Dead Day *5 | Tumor Number | Average Inhibition Weight g | Rate % |
|---|---|---|---|---|---|---|---|---|---|---|
| 1 | *1 E.C. | $ddY_F$ | 10 Control | 7 " | every fourth day every fourth day | −10 " | 21 " | 0/10 " | 1.492 3.101 | 51.9 — |

TABLE 2-continued

Result in the Intraperitoneal Administration Experiment of KGF-C

| Test | Tumor | Mouse | Amount of Administration mg *3 | Frequency of Administration | Start of Interval | Extraction Administration *4 | Dead Day *5 | Tumor Number | Average Inhibition Weight g | Rate % |
|---|---|---|---|---|---|---|---|---|---|---|
| 2 | E.C. | ddY$_F$ | 2 | 15 | every other day | +1 | 35 | 0/8 | 6.256 | 64.3 |
|  |  |  | Control | " | every other day | " | " | " | 17.534 | — |
| 3 | E.C. | ddY$_F$ | 2 | 13 | every other day | −7 | 30 | 0/10 | 3.664 | 56.7 |
|  |  |  | Control | " | every other day | " | " | 1/10 | 8.470 | — |
| 4 | S-180 | ICR | 2 | 15 | every other day | +1 | 35 | 0/10 | 6.371 | 32.8 |
|  | *2 |  | 0.05 | " | every other day | " | " | " | 1.889 | 80.1 |
|  |  |  | Control | " | every other day | " | " | " | 9.476 | — |
| 5 | S-180 | ICR | 0.25 | 15 | every day | +1 | 28 | 0/10 | 2.275 | 67.1 |
|  |  |  | 0.05 | " | " | " | " | " | 2.813 | 59.4 |
|  |  |  | Control | " | " | " | " | 0/12 | 6.921 | — |
| 6 | S-180 | ddY$_F$ | 2 | 15 | every other day | +1 | 35 | 0/8 | 2.618 | 57.9 |
|  |  |  | Control | " | every other day | " | " | " | 6.216 | — |

*1 Sarcoma S-180 tumor cell
*2 Ehrlich ascites tumor cell
*3 per mouse
*4 (−): Number of day before transplantation, (+): That after transplantation
*5 Number of day from after transplantation to extraction As is apparent from the above Tables 1 and 2, the tumor inhibiting effect of the antitumor agent of the present invention is very superior.

EXPERIMENTAL EXAMPLE

Experiment Relating to Safety and Toxicity of KGF-C

In the case of oral administration where the feed was mixed with 5% KGF-C powder and put under free ingestion, namely even in the case that such a large amount of KGF-C as 10 g/kg/day was administered every day, scarcely any difference was recognized in said properties compared with the control mouse. Also, in the case of breeding for 145 days, the body weight tended rather to increase compared with the control mouse.

Even in the case of intraperitoneal administration where a dose of KGF-C, 5 mg/mouse (250 mg/kg), was administered ten times without a break, no deaths of the mice were recognized.

In the case of KGF-C of the present invention, no adverse reaction was not recognized through all experiments in oral administration, and also in intraperitoneal administration, the body weight of test mice increased normally and no significant difference was seen in amount of ingestion of feed and water compared with the mice of the control group. Namely, during the experiment period, the growth of the transplanted tumor was observed in the course of days, and increase of body weight and as well ingestion amount of feed and water were respectively measured, and also at the time of dissection, the condition of each internal organ was observed, and relating to the property of blood, leukocyte percentage and leukocyte count were measured and variation of intestinal microflora was also sufficiently investigated, and as a result it has been confirmed that the antitumor agent of the present invention has no adverse reaction and is completely safe.

Relating to toxicity of KGF-C of the present invention, $LD_{50}$ for ddY$_F$ mouse with body weight of about 20 g was above 665 mg/kg in the case of intraperitoneal administration, and in the case that a dose of 2500 mg/kg was orally administered by compulsion, the death of mouse was not recognized at all.

What is claimed is:

1. A composition effective for the treatment of sarcoma-180 and Ehrlich carcinoma tumors, comprising a physiologically acceptable excipient and an effective amount of KGF-C having the following physical and chemical properties:
   (1) Appearance: tasteless and odorless white powder having a little hygroscopicity;
   (2) Solubility: soluble in wafer and pyridine and insoluble in alcohol, glacial acetic acid, acetone, benzene, carbon tetrachloride, chloroform, ether and tetrahydrofuran;
   (3) The pH of 1% aqueous solution is 6.89;
   (4) Sugar qualitative reaction: with respect to the 1% aqueous solution and liquid hydrolyzate thereof, Molish tests are positive in both 1% aqueous solution and 0.1% liquid hydrolyzate and Tollens reaction test is negative in 1% aqueous solution but is positive in 0.1% liquid hydrolyzate;
   (5) Specific optical rotation: $(\alpha)_D^{20} = +62.0°$ C. (C=1, water);
   (6) Sugar content: 99% is shown by phenol sulfuric acid method; KGF-C is composed of polysaccharide as principal component, and a very small amount of nitrogenous component;
   (7) Sugar composition: when KGF-C is hydrolyzed by 0.5% $H_2SO_4$ at 110° C. for 5 hours and the sugar composition is determined by thin layer chromatography and gas chromatography, the results show that it is composed of glucose and galactose in the ratio of 1:1;
   (8) Ultraviolet absorption spectrum: no particular absorption is observed;
   (9) Infrared absorption spectrum: the spectrum is shown in the drawing; and
   (10) Elemental analysis: C: 41.83%, H: 6.19%, N: 0.20%, S: below 0.2% and P: below 0.2%.

* * * * *